United States Patent [19]
Koelliker et al.

[11] Patent Number: 5,396,790
[45] Date of Patent: Mar. 14, 1995

[54] METHOD AND APPARATUS FOR THE RAPID DETERMINATION OF WATER-CEMENT RATIOS

[75] Inventors: James K. Koelliker; Mustaque Hossain, both of Manhattan, Kans.

[73] Assignee: Kansas State University Research Foundation, Manhattan, Kans.

[21] Appl. No.: 227,398

[22] Filed: Apr. 13, 1994

[51] Int. Cl.$^6$ ................... G01N 15/06; G01N 21/59
[52] U.S. Cl. ................. 73/61.72; 73/64.43; 73/54.03; 73/861.04; 73/866
[58] Field of Search ............. 73/61.72, 64.43, 54.03, 73/61.41, 861.04, 866, 64.56

[56] References Cited

U.S. PATENT DOCUMENTS

| | | | |
|---|---|---|---|
| 2,643,542 | 6/1953 | Cronk | 73/54.03 |
| 3,281,602 | 10/1966 | Keim et al. | 73/61.41 |
| 4,069,705 | 1/1978 | Burr et al. | 73/61.72 |
| 4,144,762 | 3/1979 | Duxbury | 73/866 |
| 4,196,614 | 4/1980 | McLaughlin | 73/54.03 |
| 4,615,215 | 10/1986 | Sugimoto et al. | 73/866 |
| 4,686,852 | 8/1987 | Ito et al. | 73/61.72 |
| 4,741,201 | 5/1988 | Propst | 73/61.72 |
| 4,843,868 | 7/1989 | Propst | 73/61.72 |
| 4,964,728 | 10/1990 | Kloth et al. | 73/64.43 |
| 5,237,858 | 8/1993 | Ohsaki et al. | 73/61.72 |

OTHER PUBLICATIONS

Tom; Investigation of the Rapid Analysis Machine (RAM) for Determining the Cement Content of Fresh Concrete, Apr., 1982, Technical Report SL-82-4; U.S. Army.

Gulden; Nuclear Cement Content Gage Performance Evaluation, FHWA-RD-75-525, May 1975.

Tom et al.; Evaluation of Procedures Used to Measure Cement and Water Content in Fresh Concrete; National Cooperative Highway Research Program Report 284, Jun. 1986.

*Primary Examiner*—Hezron E. Williams
*Assistant Examiner*—J. David Wiggins
*Attorney, Agent, or Firm*—Hovey, Williams, Timmons & Collins

[57] ABSTRACT

An improved turbidimeter apparatus (10) is provided for accurate, rapid, field testing of fresh concrete mixes in order to determine the water-cement ratios thereof. The apparatus (10) includes an upright sieve chamber (12) adapted to receive a concrete sample (56), together with a turbidimeter (14); a recirculation system (16) is interposed between the chamber (12) and turbidimeter (14), and permits separation of the aggregate from the concrete sample (56) and formation of a dilute dispersion suitable for turbidimetric determinations. In use, dilute water-cement dispersions are created using the apparatus (10) and turbidimeter determinations are made via turbidimeter (14); these readings can then be used with standard, previously developed water-cement ratio versus turbidimeter reading curves to accurately measure the initial water-cement ratios of concrete mixes.

18 Claims, 6 Drawing Sheets

METHOD AND APPARATUS FOR THE RAPID DETERMINATION OF WATER-CEMENT RATIOS

BACKGROUND OF THE INVENTION

1. Field of the Invention

The present invention is broadly concerned with an improved method and apparatus for the rapid, accurate determination of the water-cement ratios of fresh, uncured concrete. More particularly, the invention pertains to a method and apparatus wherein a dilute dispersion or paste of the cement fraction of the concrete is passed through a turbidimeter to determine the turbidity of the dispersion; this value can then be compared with a known, standard turbidity curve to ascertain the water-cement ratio of the fresh concrete.

2. Description of the Prior Art

Concrete is a man-made composite, usually made up of cement, aggregate and water; various types and sizes of aggregates can be used, together with additives such as air-entraining agents. Concrete is one of the most widely used of construction materials. However, concrete is unique in that it is manufactured as used and generally cannot be tested for acceptance in advance. Such acceptance is sometimes based on a strength test at an advanced stage of curing, as concrete is known to gain strength over long periods of time. Acceptance may also be based on adherence to a specified formula, along with monitoring for strength. As a consequence, concrete may be placed which may or may not be acceptable at a later date. If found unacceptable, then the emplaced concrete must be removed and new concrete poured.

Accordingly, there is a real and unsatisfied—need in the art for a means of assessing the quality of concrete before placement, and for assuring that the concrete meets the specified standards. In this regard, the water-cement ratio of a plastic, uncured concrete is known to be a good candidate for assessing the quality of concrete delivered to a construction site. This is because in engineering practice, the strength and permeability of Portland cement concrete of a given age and cured at a prescribed temperature condition is assumed to depend primarily on two factors: the water-cement ratio of the fresh concrete and the degree of compaction. Thus, when full compaction is achieved, the only variable affecting the strength and permeability of any concrete mix is the water-cement ratio. For a fully compacted concrete, this strength is taken to be inversely proportional to the water-cement ratio, according to a relationship established by Duff Abrams in 1919:

$$\text{strength}, f_c = K_1/K_2^{w/c}$$

where w/c represents the water-cement ratio of the mix, and $K_1$ and $K_2$ are empirical constants.

Although the initial water-cement ratio is the predominant factor affecting strength of a hardened concrete, there is currently no reliable method available for measuring water-cement ratios of fresh concretes in the field or at a job site. An indirect evaluation of water-cement ratio can be made through consistency or workability evaluations using a "slump" test. Although this type of test is rapid and easy to employ, it often gives very inaccurate water-cement ratio results.

Accordingly, there is an unresolved need in the art for an improved method and apparatus for the determination of water-cement ratios in concrete mixtures, especially in the field or at job sites.

SUMMARY OF THE INVENTION

The present invention overcomes the problems outlined above and provides a greatly improved method and apparatus for the determination of water-cement ratios of uncured concrete containing water, cement and aggregate. The invention permits such water-cement ratio determinations quickly and easily using a portable field tester.

Broadly speaking, the apparatus of the invention includes means for separating the aggregate from the cement and water and for creating a dilute dispersion of the cement in added water. A turbidimeter is operably coupled with the separating and diluting means for determining the turbidity of the dilute dispersions as a measure of the initial water-cement ratio. Such involves use of standard turbidity/water-cement ratio curves which are consulted to determine water-cement ratios corresponding to determined turbidities.

In more detail, the preferred apparatus includes an upright tower or chamber having sieve means therein for receiving a quantity of the uncured concrete. A shower head or similar means is provided at the upper end of the chamber for directing dilution water over uncured concrete thereby causing separation of the aggregate from the cement and water, while also creating the desired dilute dispersion. In practice, a recirculation conduit is coupled between the bottom and top of the upright chamber so as to permit recirculation of the dilution water over time; to this end, a pump is interposed within this conduit.

The turbidimeter is advantageously coupled to the recirculation conduit of the apparatus, and appropriate valving is provided for directing the dilute water-cement dispersion through the turbidimeter for successive turbidity determinations. Although a variety of turbidimeters can be employed, DRT turbidimeters commercialized by H. F. Scientific, Inc. of Ft. Myers, Fla. have been found to be satisfactory. In this connection, turbidity is an expression of the optical properties that cause light to be scattered or passed through a liquid sample, and is largely a function of the refractive index, and the size and shape of particles in the liquid. Therefore, the particular turbidity results achieved may be dependent upon the instrument employed.

Generally, the water-cement ratios of the dilute dispersions tested for turbidity according to the invention should be in the range of from about 10–1000, and more preferably from about 50–250. Furthermore, it may be advisable to take multiple turbidity readings over time to insure that the most accurate results are obtained.

DETAILED DESCRIPTION OF THE PREFERRED EMBODIMENTS

Figure 1:
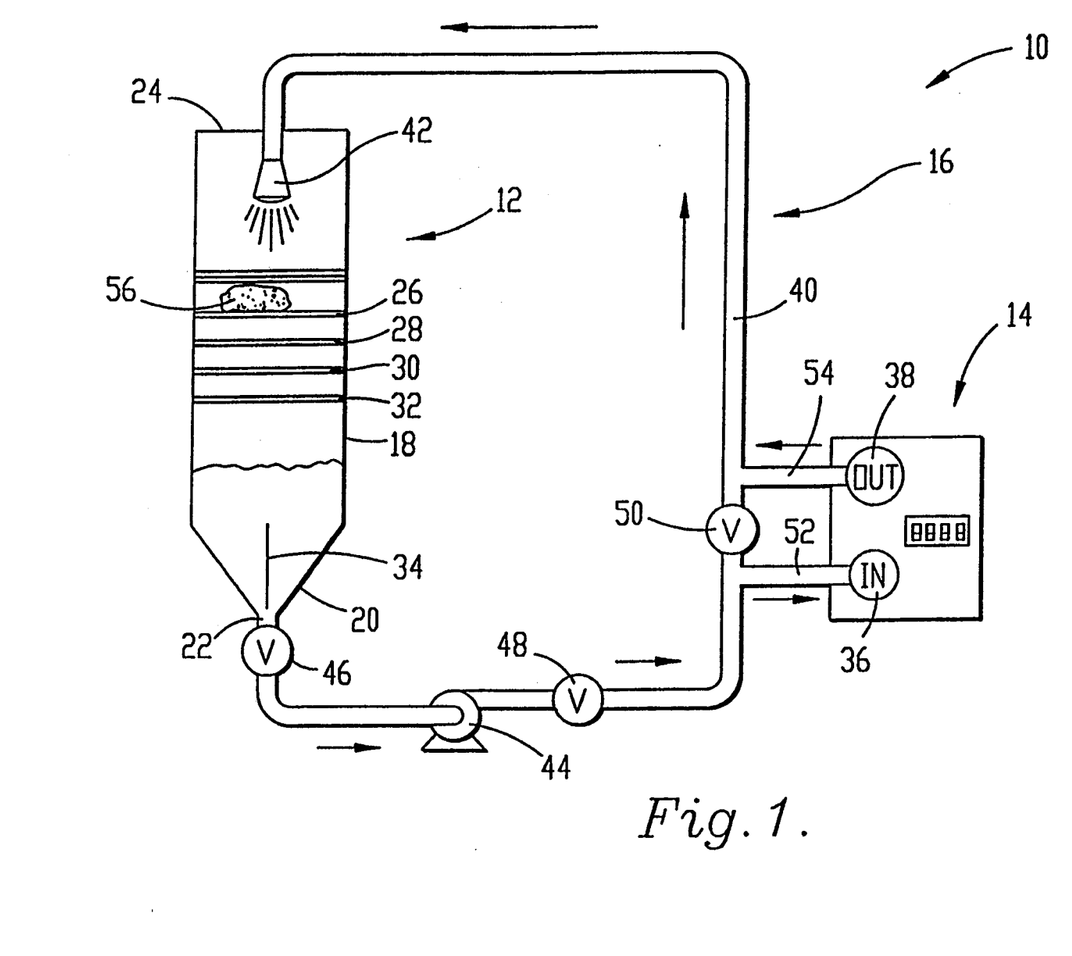
FIG. 1 is a schematic representation of the preferred apparatus for determining water-cement ratios of fresh concrete mixtures.

Turning now to the drawings, and particularly FIG. 1, an apparatus 10 for determining the water-cement ratio of uncured concrete containing water, cement and aggregate is illustrated. Broadly speaking, the apparatus 10 includes an upright chamber or tower 12, a turbidimeter 14 and a recirculation system 16.

In more detail, the tower 12 is an upright metallic unit presenting a generally cylindrical main body 18 terminating in a lowermost conical bottom section 20, the latter presenting a tubular outlet 22. The upper end of body 18 has a top wall 24 which is apertured to receive the upper end of a recirculation conduit as will be described. The body 18 houses a plurality of transversely extending, vertically stacked sieves 26, 28, 30, 32. These sieves are preferably, in vertically descending order, #4, #10, #50 and #100 sieves. The lowermost conical section 20 of the chamber 12 includes an upright, central anti-vortex plate 34 adjacent outlet 22.

The turbidimeter 14 is a commercially available unit, specifically a DRT-100B turbidimeter sold by H. F. Scientific, Inc. of Ft. Myers, Fla.. The turbidimeter includes respective inlet and outlet ports 36, 38 in order to permit passage of liquid through the turbidimeter and turbidimeter determinations using the apparatus 14.

Recirculation system 16 includes a primary conduit 40 extending from outlet 22 of chamber 12 upwardly through top wall 24 and terminating in a dispersing outlet or showerhead 42 situated within the confines of chamber 12 above the stacked sieves 26–32. A pump 44 (in practice a ½ hp, 24 gpm pump) is interposed in main conduit 40, along with spaced valves 46, 48 and 50. The overall recirculation system 16 further includes a conduit 52 upstream of valve 50 and communicating with turbidimeter inlet 36; and a conduit 54 operatively coupled between turbidimeter outlet 38 and main conduit 40 downstream of valve 50.

In the use of apparatus 10, a known quantity of fresh concrete 56 is placed within chamber 12 (which is provided with an access door for this purpose) above the stacked sieves 26–32. Next, a known amount of water is charged to the chamber 12 to fill the lower portion 20 thereof. At this-point, valves 46, 48 and 50 are opened and pump 44 is actuated, thereby circulating water through main conduit 40 and showerhead 42, this serving to wash the concrete 56 through the sieve system to remove the aggregate from the concrete. After such recirculation has proceeded for a time sufficient to assure substantial separation of the aggregate, the valve 50 is closed, thereby diverting the recirculating, dilute stream of cement and water through turbidimeter 14 via conduits 52, 54 and corresponding inlet and outlet 36, 38. During passage of the dilute dispersion through the turbidimeter 14, readings may be taken at successive time intervals until a substantial steady state is achieved. Generally speaking, a measurement time period of up to about 300 seconds has been found to be sufficient. At this point, the resultant turbidimeter reading can be compared with a standard graph of turbidimeters readings versus water-cement ratios (similar to that shown in FIG. 6) in order to permit an accurate determination of the initial water-cement ratio of the starting concrete.

The following examples illustrate preferred embodiments of the invention and use thereof. It is to be understood, however, that these examples are presented by way of illustration only and nothing therein should be taken as a limitation upon the overall scope of the invention.

EXAMPLE 1

In this series of tests, non air-entrained concrete mix having water/cement ratios of 0.40, 0.44 and 0.48 were tested in the FIG. 1 apparatus to determine their turbidities over time. In each case, fresh concrete was made using a 1:2:3 mixture of cement, fine aggregate, and coarse aggregate (1 lb. cement, 2 lbs. fine aggregate, 3 lbs. coarse aggregate) with the appropriate quantity of water to achieve the respective water/cement ratio.

In each test, 20 lbs. of wash water was used by addition thereof to the conical base of the wash tower. The fresh concrete was allowed to stand for 19 minutes before the test began, and a 1 lb. sample of the concrete was placed on the uppermost sieve. The water was then circulated through the wash tower and turbidimeter, and readings were taken at specified elapsed times.

The following tables set forth the results of these tests, wherein two separate batches of concrete at each water/cement ratio were run.

TABLE 1

| Water/Cement Ratio = 0.40 | | | | |
|---|---|---|---|---|
| Trial No. | | 1 | 2 | |
| Water-cement ratio | | 0.40 | 0.40 | |
| Wt. of cement (g) | | 4268 | 4268 | |
| Wt. of water (g) | | 1707 | 1707 | |
| Wt. of fine aggregate (g) | | 8537 | 8537 | |
| Wt. of coarse aggregate (g) | | 12805 | 12805 | |
| Total wt. of mix (g) | | 27317 | 27317 | |
| Wt. of water in the 1-lb. sample (g) | | 28 | 28 | |
| Wt. of wash water (g) | | 9072 | 9072 | |
| Dilution (approximate) | | 320 | 320 | |
| | Elapsed Time (sec) | Batch 1 | Batch 2 | Average | Std. Dev. |
| Turbidimeter Readings (NTU)* | 0 | 4 | 4 | 4 | 0 |
| | 60 | 322 | 325 | 324 | 2 |
| | 120 | 223 | 222 | 223 | 1 |
| | 150 | 208 | 213 | 211 | 4 |
| | 180 | 195 | 201 | 198 | 4 |
| | 210 | 188 | 197 | 193 | 6 |
| | 225 | 187 | 198 | 193 | 8 |
| | 240 | 183 | 198 | 191 | 11 |

TABLE 1-continued

| Water/Cement Ratio = 0.40 | | | | |
|---|---|---|---|---|
| 255 | 183 | 198 | 191 | 11 |
| 270 | 182 | 201 | 192 | 13 |
| 285 | 184 | 204 | 194 | 14 |
| 300 | 178 | 205 | 192 | 19 |
| 315 | 178 | 208 | 193 | 21 |
| 330 | 179 | 183 | 181 | 3 |
| 345 | 181 | 180 | 181 | 1 |
| 360 | 179 | 174 | 177 | 4 |

*Nephelometric Turbidity Unit

TABLE 2

| Water/Cement Ratio = 0.44 | | | | | |
|---|---|---|---|---|---|
| Trial No. | | 1 | 2 | | |
| Water-cement ratio | | 0.44 | 0.44 | | |
| Wt. of cement (g) | | 4268 | 4268 | | |
| Wt. of water (g) | | 1878 | 1878 | | |
| Wt. of fine aggregate (g) | | 8537 | 8537 | | |
| Wt. of coarse aggregate (g) | | 12805 | 12805 | | |
| Total wt. of mix (g) | | 27488 | 27488 | | |
| Wt. of water in the 1-lb. sample (g) | | 31 | 31 | | |
| Wt. of wash water (g) | | 9072 | 9072 | | |
| Dilution (approximate) | | 293 | 293 | | |
| | Elapsed Time (sec) | Batch 1 | Batch 2 | Average | Std. Dev. |
| Turbidimeter Readings | 0 | 5 | 4 | 5 | 1 |
| (NTU)* | 60 | 348 | 342 | 345 | 4 |
| | 120 | 245 | 255 | 250 | 7 |
| | 150 | 235 | 228 | 232 | 5 |
| | 180 | 221 | 220 | 221 | 1 |
| | 210 | 217 | 205 | 211 | 8 |
| | 225 | 215 | 205 | 210 | 7 |
| | 240 | 219 | 202 | 211 | 12 |
| | 255 | 205 | 198 | 202 | 5 |
| | 270 | 203 | 203 | 203 | 0 |
| | 285 | 202 | 205 | 204 | 2 |
| | 300 | 208 | 210 | 209 | 1 |
| | 315 | 208 | 209 | 209 | 1 |
| | 330 | 202 | 211 | 207 | 6 |
| | 345 | 205 | 194 | 200 | 8 |
| | 360 | 207 | 197 | 202 | 7 |

*Nephelometric Turbidity Unit

TABLE 3

| Water/Cement Ratio = 0.48 | | | | | |
|---|---|---|---|---|---|
| Trial No. | | 1 | 2 | | |
| Water-cement ratio | | 0.48 | 0.48 | | |
| Wt. of cement (g) | | 4268 | 4268 | | |
| Wt. of water (g) | | 2049 | 2049 | | |
| Wt. of fine aggregate (g) | | 8537 | 8537 | | |
| Wt. of coarse aggregate (g) | | 12805 | 12805 | | |
| Total wt. of mix (g) | | 27659 | 27659 | | |
| Wt. of water in the 1-lb. sample (g) | | 34 | 34 | | |
| Wt. of wash water (g) | | 9072 | 9072 | | |
| Dilution (approximate) | | 270 | 270 | | |
| | Elapsed time (sec) | Batch 1 | Batch 2 | Average | Std. Dev. |
| Turbidimeter Readings | 0 | 4 | 4 | 4 | 0 |
| (NTU)* | 60 | 253 | 348 | 301 | 67 |
| | 120 | 245 | 265 | 255 | 14 |
| | 150 | 244 | 262 | 253 | 13 |
| | 180 | 236 | 244 | 240 | 6 |
| | 210 | 236 | 235 | 236 | 1 |
| | 225 | 233 | 235 | 234 | 1 |
| | 240 | 233 | 235 | 234 | 1 |
| | 255 | 232 | 227 | 230 | 4 |
| | 270 | 234 | 227 | 230 | 5 |
| | 285 | 229 | 234 | 232 | 4 |
| | 300 | 229 | 237 | 233 | 6 |
| | 315 | 227 | 236 | 232 | 6 |
| | 330 | 228 | 213 | 221 | 11 |
| | 345 | 227 | 214 | 221 | 9 |
| | 360 | 231 | 209 | 220 | 16 |

*Nephelometric Turbidity Unit

Figure 2:
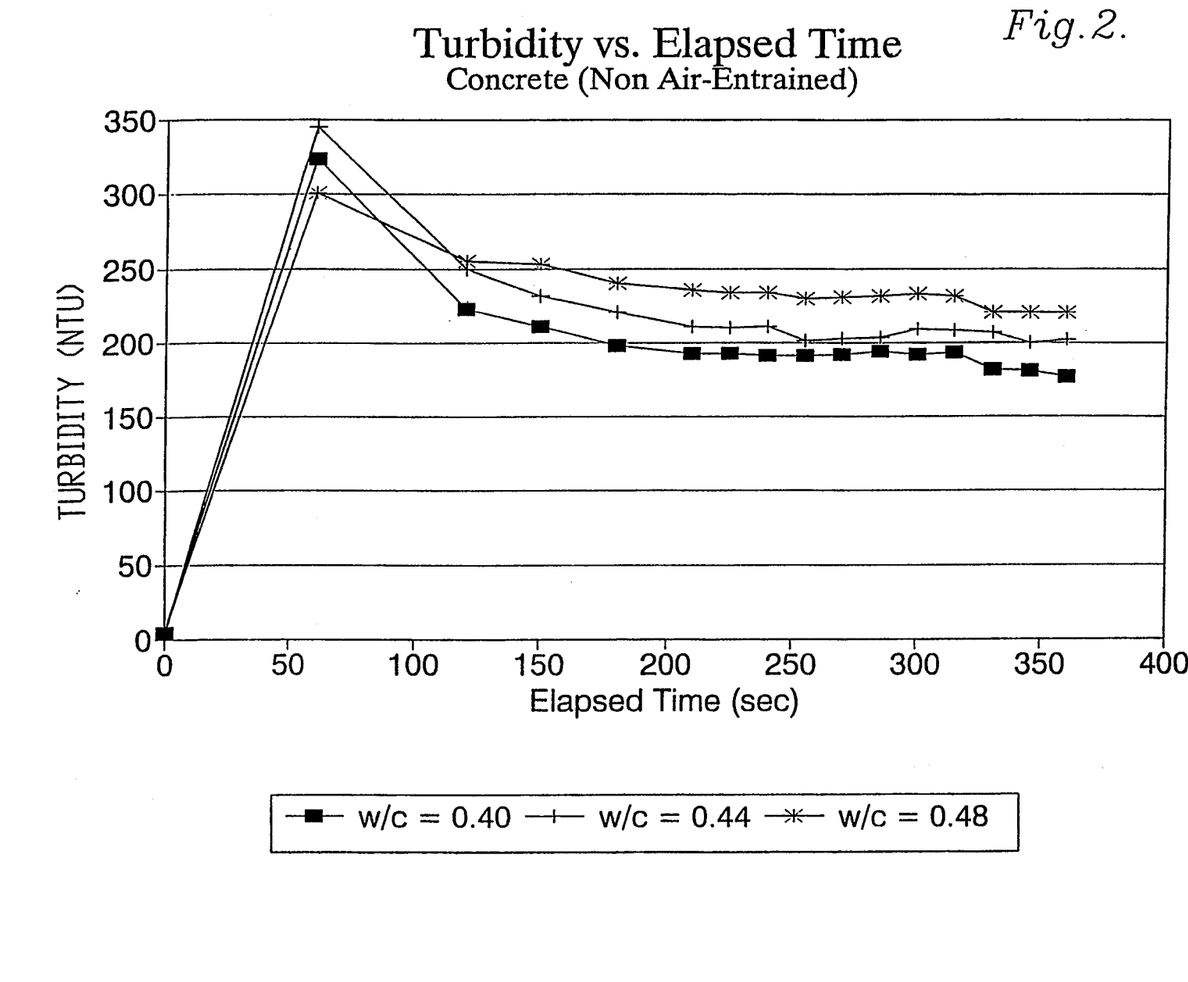
FIG. 2 is a graph of average turbidities versus elapsed time for the non air-entrained concrete mixtures tested in Example 1.

FIG. 2 is a graphical representation of the average turbidities versus elapsed time for the non air-entrained concrete mixtures described above. As can be seen, the average values are quite consistent, particularly above about 200 seconds elapsed time.

EXAMPLE 2

In another series of tests similar to those described above, concretes having water/cement ratios of 0.4, 0.44 and 0.48 were prepared which also included an amount of an air entrainment surfactant (Vinsol Resin sold by Fritz Chemical, Dallas, Tex.). Such air entrainment agents are quite conventional and are typically used with concretes which must be poured and cured in cold weather.

The tests were performed in the same manner as Example 1, save for the fact that the surfactant was added to the concrete during initial mixing thereof.

The following tables set forth the results of these tests.

TABLE 4

| Water/Cement Ratio = 0.40 + Surfactant | | | | | |
|---|---|---|---|---|---|
| Trial No. | | 1 | 2 | | |
| Water-cement ratio | | 0.40 | 0.40 | | |
| Wt. of cement (g) | | 4268 | 4268 | | |
| Wt. of water (g) | | 1707 | 1707 | | |
| Wt. of fine aggregate (g) | | 8537 | 8537 | | |
| Wt. of coarse aggregate (g) | | 12805 | 12805 | | |
| Vol. of air-entrainer in concrete (ml) | | 3.00 | 3.00 | | |
| Total wt. of mix (g) | | 27317 | 27317 | | |
| Wt. of water in the 1-lb. sample (g) | | 28 | 28 | | |
| Wt. of wash water (g) | | 9072 | 9072 | | |
| Dilution (approximate) | | 320 | 320 | | |
| | Elapsed Time (sec) | Batch 1 | Batch 2 | Average | Std. Dev. |
| Turbidimeter Readings (NTU)* | 0 | 4 | 4 | 4 | 0 |
| | 60 | 412 | 364 | 388 | 34 |
| | 120 | 295 | 259 | 277 | 25 |
| | 150 | 269 | 233 | 251 | 25 |
| | 180 | 249 | 221 | 235 | 20 |
| | 210 | 236 | 208 | 222 | 20 |
| | 225 | 233 | 203 | 218 | 21 |
| | 240 | 228 | 204 | 216 | 17 |
| | 255 | 227 | 209 | 218 | 13 |
| | 270 | 225 | 216 | 221 | 6 |
| | 285 | 220 | 218 | 219 | 1 |
| | 300 | 216 | 218 | 217 | 1 |
| | 315 | 218 | 217 | 218 | 1 |
| | 330 | 218 | 220 | 219 | 1 |
| | 345 | 216 | 205 | 211 | 8 |
| | 360 | 218 | 204 | 211 | 10 |

*Nephelometric Turbidity Unit

| Water/Cement Ratio = 0.44 + Surfactant | | | | | |
|---|---|---|---|---|---|
| Trial No. | | 1 | 2 | | |
| Water-cement ratio | | 0.44 | 0.44 | | |
| Wt. of cement (g) | | 4268 | 4268 | | |
| Wt. of water (g) | | 1878 | 1878 | | |
| Wt. of fine aggregate (g) | | 8537 | 8537 | | |
| Wt. of coarse aggregate (g) | | 12805 | 12805 | | |
| Vol. of air-entrainer in concrete (ml) | | 3.00 | 3.00 | | |
| Total wt. of mix (g) | | 27488 | 27488 | | |
| Wt. of water in the 1-lb. sample (g) | | 31 | 31 | | |
| Wt. of wash water (g) | | 9072 | 9072 | | |
| Dilution (approximate) | | 293 | 293 | | |
| | Elapsed Time (sec) | Batch 1 | Batch 2 | Average | Std. Dev. |
| Turbidimeter Readings (NTU)* | 0 | 4 | 5 | 5 | 1 |
| | 60 | 301 | 337 | 319 | 25 |
| | 120 | 222 | 216 | 219 | 4 |
| | 150 | 206 | 203 | 205 | 2 |
| | 180 | 194 | 197 | 196 | 2 |
| | 210 | 189 | 190 | 190 | 1 |
| | 225 | 190 | 187 | 189 | 2 |
| | 240 | 192 | 186 | 189 | 4 |
| | 255 | 188 | 186 | 187 | 1 |
| | 270 | 188 | 185 | 187 | 2 |
| | 285 | 187 | 191 | 189 | 3 |
| | 300 | 183 | 189 | 186 | 4 |
| | 315 | 181 | 190 | 186 | 6 |
| | 330 | 184 | 190 | 187 | 4 |
| | 345 | 181 | 192 | 187 | 8 |
| | 360 | 186 | 198 | 192 | 8 |

*Nephelometric Turbidity Unit

TABLE 6

| Water/Cement Ratio = 0.48 + Surfactant | | |
| --- | --- | --- |
| Trial No. | 1 | 2 |
| Water-cement ratio | 0.48 | 0.48 |
| Wt. of cement (g) | 4268 | 4268 |
| Wt. of water (g) | 2049 | 2049 |
| Wt. of fine aggregate (g) | 8537 | 8537 |
| Wt. of coarse aggregate (g) | 12805 | 12805 |
| Vol. of air-entrainer in concrete (ml) | 3.00 | 3.00 |
| Total wt. of mix (g) | 27659 | 27659 |
| Wt. of water in the 1-lb. sample (g) | 34 | 34 |
| Wt. of wash water (g) | 9072 | 9072 |
| Dilution (approximate) | 270 | 270 |

| | Elapsed Time (sec) | Batch 1 | Batch 2 | Average | Std. Dev. |
| --- | --- | --- | --- | --- | --- |
| Turbidimeter Readings (NTU)* | 0 | 5 | 5 | 5 | 0 |
| | 60 | 233 | 256 | 245 | 16 |
| | 120 | 194 | 176 | 185 | 13 |
| | 150 | 189 | 180 | 185 | 6 |
| | 180 | 183 | 179 | 181 | 3 |
| | 210 | 183 | 178 | 181 | 4 |
| | 225 | 185 | 181 | 183 | 3 |
| | 240 | 185 | 177 | 181 | 6 |
| | 255 | 186 | 180 | 183 | 4 |
| | 270 | 183 | 180 | 182 | 2 |
| | 285 | 189 | 180 | 185 | 6 |
| | 300 | 187 | 177 | 182 | 7 |
| | 315 | 192 | 180 | 186 | 8 |
| | 330 | 200 | 182 | 191 | 13 |
| | 345 | 207 | 185 | 196 | 16 |
| | 360 | 211 | 198 | 205 | 9 |

*Nephelometric Turbidity Unit

Figure 3:
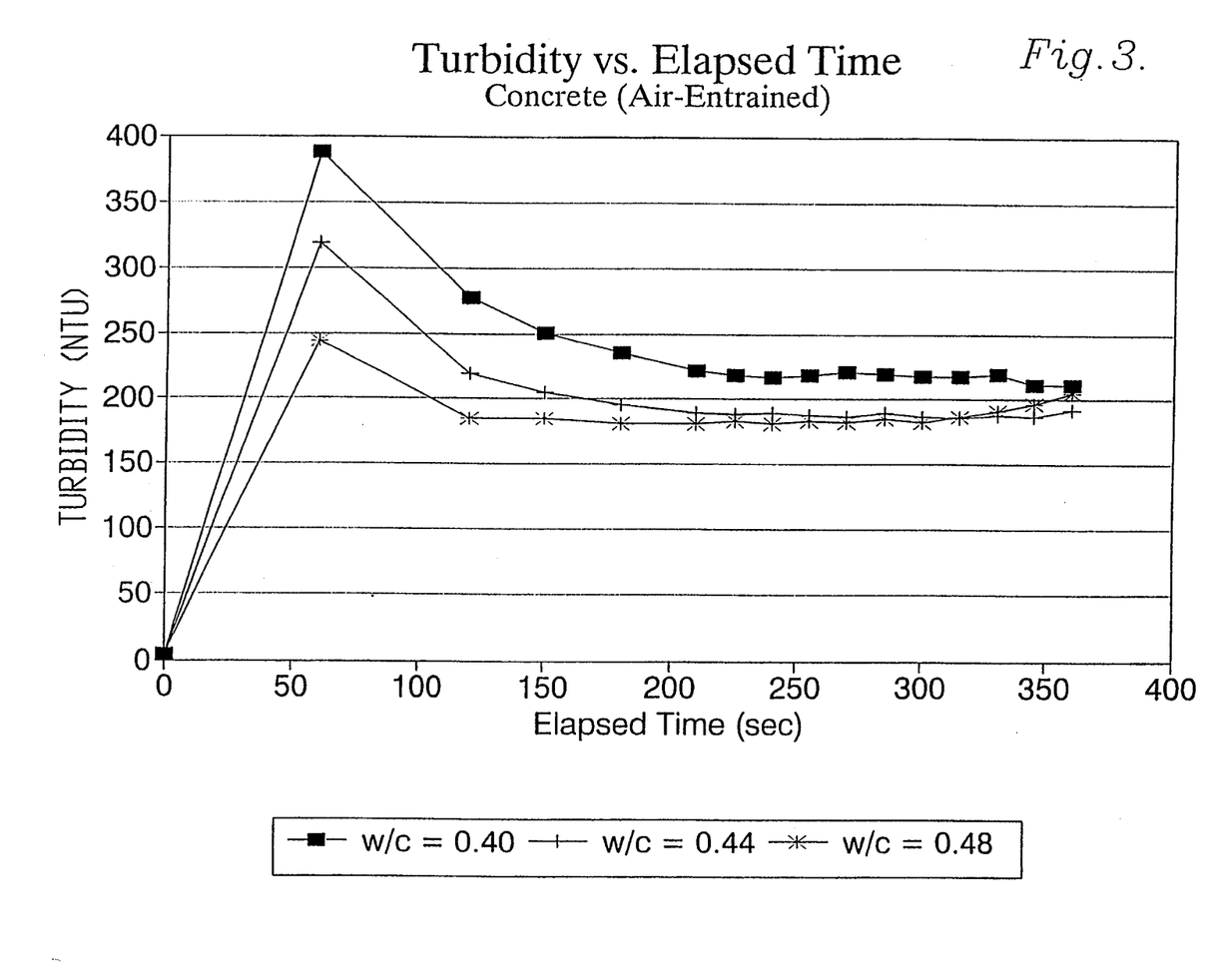
FIG. 3 is a graph of average turbidities versus elapsed time for the concretes with air-entraining agent tested in Example 2.

FIG. 3 is a graph of the average turbidities obtained in these tests versus elapsed time. As can be seen from a comparative study of FIGS. 2 and 3, the average turbidities were lowered (and inconsisted) in the case of the air-entrained concretes.

EXAMPLE 3

In another series of tests, concretes identical with those tested in Example 2 were further supplemented with one or two air detraining agents, namely tributyl phosphate (TBP) at a level of 20 milliliters, and polypropylene glycol (PPG) at a level of about 2 milliliters. The PPG had an average molecular weight of about 2,000, and was obtained from BASF Corp. Chemical Div., Parsippany, N.J. under the trade designation "PLURADYNE" No. DB1021. The air-detraining agents were added to the 20 lbs. of wash water at the beginning of each test run.

The purpose of these tests was to determine whether an air detraining agent could be used with air-entrained concretes to obtain valid water/cement test results.

The following tables set forth the data recorded in this series of tests, and also include the average data from the corresponding tables of Examples 1 and 2.

TABLE 7

| Water/Cement Ratio = 0.40 + Surfactant + Air Detrainer | | | | |
| --- | --- | --- | --- | --- |
| Trial No. | 1 | 2 | Air Entrained | Non Air-Entrained mix |
| Water-cement ratio | 0.40 | 0.40 | 0.40 | 0.40 |
| Wt. of cement (g) | 4268 | 4268 | 4268 | 4268 |
| Wt. of water (g) | 1707 | 1707 | 1707 | 1707 |
| Wt. of fine aggregate (g) | 8537 | 8537 | 8537 | 8537 |
| Wt. of coarse aggregate (g) | 12805 | 12805 | 12805 | 12805 |
| Vol. of air-entrainer in concrete (ml) | 3.00 | 3.00 | 3.00 | 3.00 |
| Total wt. of mix (g) | 27317 | 27317 | 27317 | 27317 |
| Wt. of water in the 1-lb. sample (g) | 28 | 28 | 28 | 28 |
| Wt. of wash water (g) | 9072 | 9072 | 9072 | 9072 |
| Vol. of air-detrainer in wash water (ml) | 20.00 (TBP) | 20.00 (PPG) | 0.00 | 0.00 |
| Dilution (approximate) | 320 | 320 | 320 | 320 |

| | Elapsed Time (sec) | Batch 1 | Batch 2 | (Avg) | (Avg) |
| --- | --- | --- | --- | --- | --- |
| Turbidimeter Readings (NTU)* | 0 | 4 | 4 | 4 | 4 |
| | 60 | 296 | 313 | 388 | 324 |
| | 120 | 209 | 229 | 277 | 223 |
| | 150 | 199 | 217 | 251 | 211 |
| | 180 | 190 | 204 | 235 | 198 |
| | 210 | 186 | 193 | 222 | 193 |
| | 225 | 179 | 194 | 218 | 193 |
| | 240 | 185 | 192 | 216 | 191 |
| | 255 | 186 | 189 | 218 | 191 |
| | 270 | 184 | 188 | 221 | 192 |
| | 285 | 182 | 186 | 219 | 194 |

TABLE 7-continued

| Water/Cement Ratio = 0.40 + Surfactant + Air Detrainer | | | | |
|---|---|---|---|---|
| 300 | 183 | 183 | 217 | 192 |
| 315 | 177 | 185 | 218 | 193 |
| 330 | 181 | 180 | 219 | 181 |
| 345 | 182 | 180 | 211 | 181 |
| 360 | 180 | 178 | 211 | 177 |

*Nephelometric Turbidity Unit

TABLE 8

| Water/Cement Ratio = 0.44 + Surfactant + Air Detrainer | | | | | | | |
|---|---|---|---|---|---|---|---|
| Trial No. | | 1 | 2 | | | Air-En-trained | Non Air-Entrained Mix |
| Water-cement ratio | | 0.44 | 0.44 | | | 0.44 | 0.44 |
| Wt. of cement (g) | | 4268 | 4268 | | | 4268 | 4268 |
| Wt. of water (g) | | 1878 | 1878 | | | 1878 | 1878 |
| Wt. of fine aggregate (g) | | 8537 | 8537 | | | 8537 | 8537 |
| Wt. of coarse aggregate (g) | | 12805 | 12805 | | | 12805 | 12805 |
| Vol. of air-entrainer in concrete (ml) | | 3.00 | 3.00 | | | 3.00 | 0.00 |
| Total wt. of mix (g) | | 27488 | 27488 | | | 27488 | 27488 |
| Wt. of water in the 1-lb. sample (g) | | 31 | 31 | | | 31 | 31 |
| Wt. of wash water (g) | | 9072 | 9072 | | | 9072 | 9072 |
| Vol. of air-detrainer in wash water (ml) | | 2.00 (PPG) | 2.00 (PPG) | | | 0.00 | 0.00 |
| Dilution (approximate) | | 293 | 293 | | | 293 | 293 |
| | Elapsed Time (sec) | Batch 1 | Batch 2 | Aver-age | Std. Dev. | (Avg) | (Avg) |
| Turbidimeter Readings (NTU) | 0 | 5 | 4 | 5 | 1 | 5 | 5 |
| | 60 | 366 | 325 | 346 | 29 | 319 | 345 |
| | 120 | 267 | 257 | 262 | 7 | 219 | 250 |
| | 150 | 239 | 244 | 242 | 4 | 205 | 232 |
| | 180 | 232 | 233 | 233 | 1 | 196 | 221 |
| | 210 | 216 | 226 | 221 | 7 | 190 | 211 |
| | 225 | 216 | 222 | 219 | 4 | 189 | 210 |
| | 240 | 218 | 219 | 219 | 1 | 189 | 211 |
| | 255 | 217 | 218 | 218 | 1 | 187 | 202 |
| | 270 | 204 | 214 | 209 | 7 | 187 | 203 |
| | 285 | 207 | 217 | 212 | 7 | 189 | 204 |
| | 300 | 209 | 213 | 211 | 3 | 186 | 209 |
| | 315 | 208 | 212 | 210 | 3 | 186 | 209 |
| | 330 | 203 | 209 | 206 | 4 | 187 | 207 |
| | 345 | 206 | 208 | 207 | 1 | 187 | 200 |
| | 360 | 298 | 208 | 203 | 7 | 192 | 202 |

TABLE 9

| Water/Cement Ratio = 0.48 + Surfactant + Air Detrainer | | | | | | | |
|---|---|---|---|---|---|---|---|
| Trial No. | | 1 | 2 | | | Air-En-trained | Non Air-Entrained Mix |
| Water-cement ratio | | 0.48 | 0.48 | | | 0.48 | 0.48 |
| Wt. of cement (g) | | 4268 | 4268 | | | 4268 | 4268 |
| Wt. of water (g) | | 2049 | 2049 | | | 2049 | 2049 |
| Wt. of fine aggregate (g) | | 8537 | 8537 | | | 8537 | 8537 |
| Wt. of coarse aggregate (g) | | 12805 | 12805 | | | 12805 | 12805 |
| Vol. of air-entrainer in concrete (ml) | | 3.00 | 3.00 | | | 3.00 | 0.00 |
| Total wt. of mix (g) | | 27659 | 27659 | | | 27659 | 27659 |
| Wt. of water in the 1-lb. sample (g) | | 34 | 34 | | | 34 | 34 |
| Wt. of wash water (g) | | 9072 | 9072 | | | 9072 | 9072 |
| Vol. of air-detrainer in wash water (ml) | | 2.00 (PPG) | 2.50 (PPG) | | | 0.00 | 0.00 |
| Dilution (approximate) | | 270 | 270 | | | 270 | 270 |
| | Elapsed Time (sec) | Batch 1 | Batch 2 | Aver-age | Std. Dev. | 11/25/93 (Avg) | 12/2/93 (Avg) |
| Turbidimeter Readings (NTU)* | 0 | 5 | 4 | 5 | 1 | 5 | 4 |
| | 60 | 408 | 300 | 354 | 76 | 245 | 301 |
| | 120 | 312 | 246 | 279 | 47 | 185 | 255 |
| | 150 | 295 | 243 | 269 | 37 | 185 | 253 |
| | 180 | 285 | 243 | 264 | 30 | 181 | 240 |
| | 210 | 276 | 232 | 254 | 31 | 181 | 236 |
| | 225 | 264 | 240 | 252 | 17 | 183 | 234 |
| | 240 | 258 | 236 | 247 | 16 | 181 | 234 |
| | 255 | 252 | 228 | 240 | 17 | 183 | 230 |
| | 270 | 248 | 232 | 240 | 11 | 182 | 231 |
| | 285 | 238 | 231 | 235 | 5 | 185 | 232 |
| | 300 | 231 | 231 | 231 | 0 | 182 | 233 |
| | 315 | 236 | 228 | 232 | 6 | 186 | 232 |

TABLE 9-continued

| Water/Cement Ratio = 0.48 + Surfactant + Air Detrainer | | | | | | |
|---|---|---|---|---|---|---|
| 330 | 224 | 225 | 225 | 1 | 191 | 221 |
| 345 | 222 | 227 | 225 | 4 | 196 | 221 |
| 360 | 227 | 226 | 227 | 1 | 205 | 220 |

*Nephelometric Turbidity Unit

Figure 4:
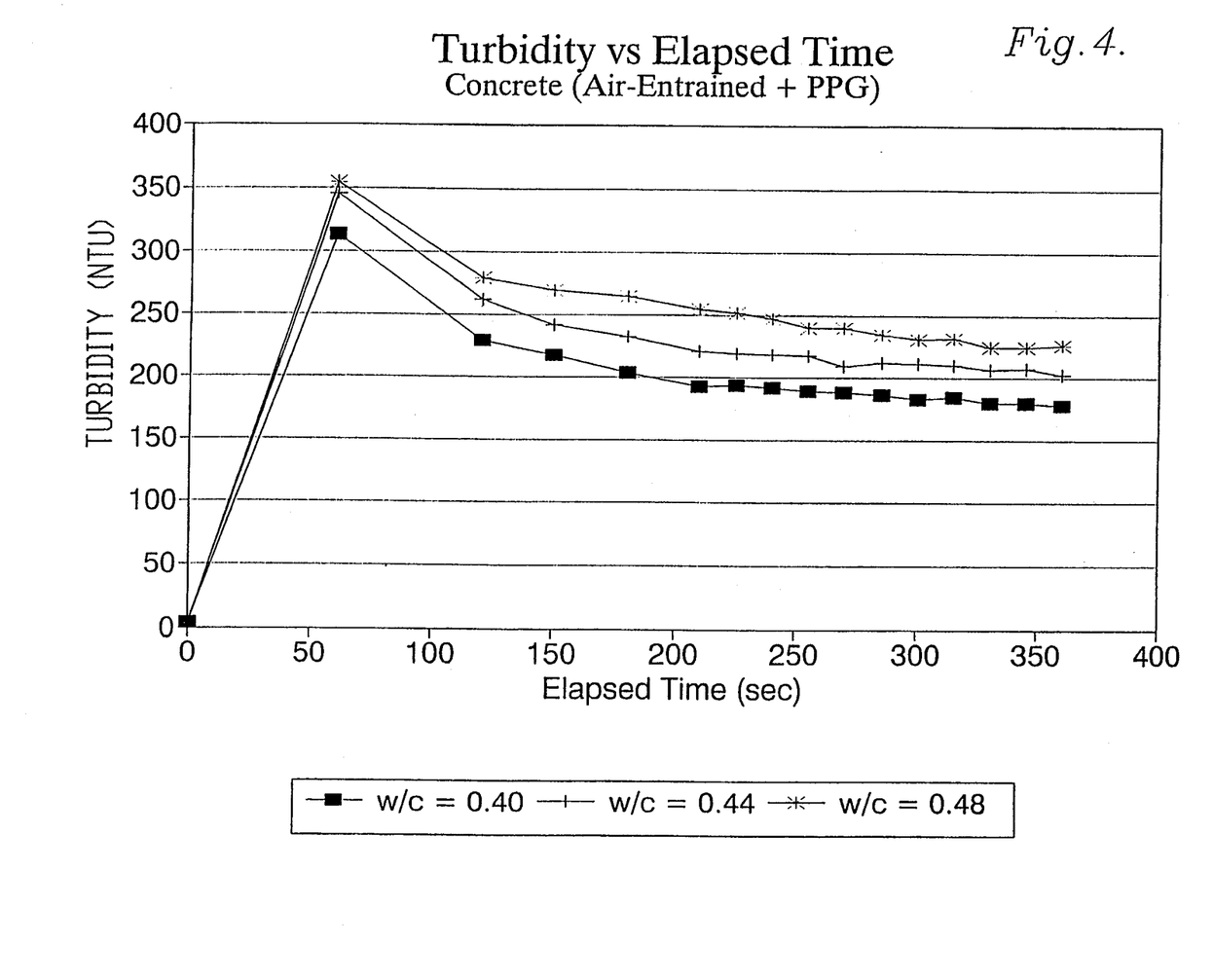
FIG. 4 is a graph of average turbidities versus elapsed time for the concretes with air-entraining agent and polypropylene glycol tested in Example 3.
Figure 5:
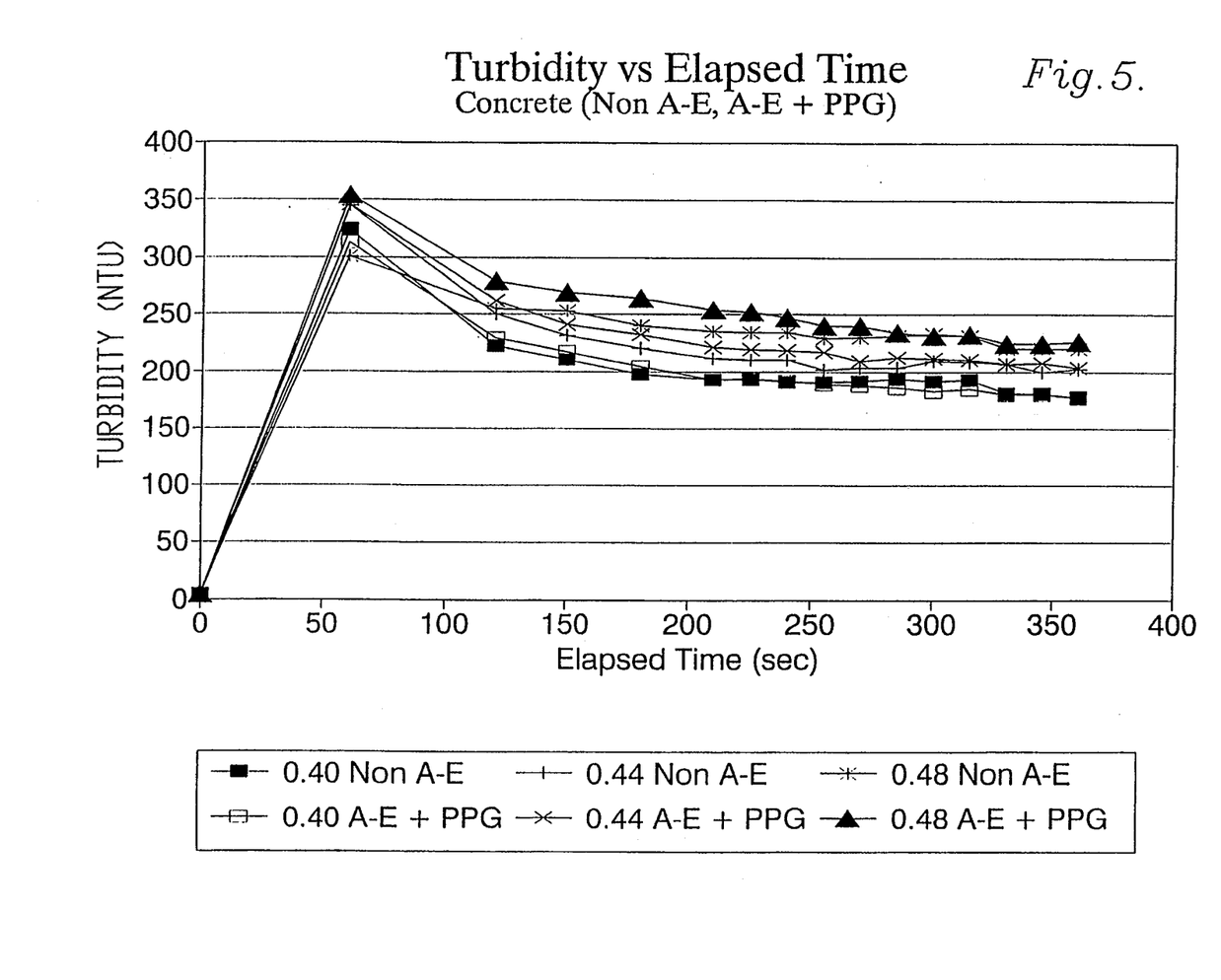
FIG. 5 is a graph of average turbidities versus elapsed time for non air-entrained concrete and concrete with air-entrainer and polypropylene glycol.

FIG. 4 is a graph of the average turbidities versus elapsed time for the PPG tests of this example. This graph illustrates that the use of an air detraining agent such as PPG substantially eliminates the effect of an air entrainment agent in the concrete mixes, thereby permitting accurate water/cement determinations. This effect is further confirmed by the graph of FIG. 5, which illustrates average turbidities versus elapsed time for both the non air-entrained concrete and air entrained plus PPG concrete mixes. As can be seen, the data points for all of these mixes are sufficiently close to permit essentially accurate water/cement ratio determinations. Thus, use of PPG or a similar air detraining agent results in accurate water/cement ratio determinations even when the concrete being tested includes an air entrainment agent.

EXAMPLE 4

In another series of tests, turbidimeter readings were taken for water-cement pastes having initial water-cement ratios varying from 0.35-0.50, with dilution ratios of 1:10 (for each gram of water in the paste, an additional 10 grams of water was added), 1:100 and 1:1000. The turbidimeter used was a DRT-100B unit commercialized by H. F. Scientific, Inc. of Ft. Myers, Fla. (an instruction manual entitled "DRT-100B & DRT-100B RESEARCH TURBIDIMETERS" provided by the manufacturer is incorporated by reference herein and explains the construction and operation of this preferred turbidimeter). In each case, the known water-cement dilution was prepared by mixing cement and water in a beaker, followed by stirring using an automatic dispersion mixer for 30 seconds. The dilution was then transferred to the turbidimeter cuvette as quickly as possible, and three readings were taken. All readings were taken within 60 seconds after the dilution was placed in the cuvette, as it was observed that any further delay resulted in a lower reading.

Table 10 sets forth the results of these tests and indicates that the 1:100 dilution ratio provided the most consistent turbidimeter readings in the range 0 to 100 NTU (Nephelometric Turbidity Unit). Based upon these results, 0-100 NTU and 1:100 dilution ratios were selected for further investigations.

TABLE 10

Turbidimeter Readings of Cement for Different Ranges of Turbidimeter for Different Dilution Ratios

| Sample No. | w/c ratio | Turbidimeter reading (range) | | | |
|---|---|---|---|---|---|
| | | 1 | 10 | 100 | 1000 |
| Dilution 1:10 | | | | | |
| 1 | 0.35 | 0.85 | 0.76 | 0.7 | 1 |
| 2 | 0.40 | 0.85 | 0.81 | 0.8 | 0 |
| 3 | 0.45 | 0.82 | 0.68 | 0.8 | 0 |
| 4 | 0.50 | 0.84 | 0.57 | 0.5 | 0 |
| Dilution 1:100 | | | | | |
| 1 | 0.35 | 1.20 | 2.24 | 2.1 | 2 |
| 2 | 0.40 | 1.73 | 5.21 | 5.3 | 5 |
| 3 | 0.45 | 1.00 | 9.45 | 10.2 | 10 |
| 4 | 0.50 | 1.00 | 11.11 | 15.4 | 14 |
| Dilution 1:1000 | | | | | |
| 1 | 0.35 | 1.00 | 1.00 | 1.0 | 485 |
| 2 | 0.40 | 1.00 | 1.00 | 1.0 | 502 |
| 3 | 0.45 | 1.00 | 1.00 | 1.0 | 444 |
| 4 | 0.50 | 1.00 | 1.00 | 1.0 | 42.5 |

Next, an experiment was designed to determine any statistically valid correlation which might be present between the water-cement ratio of the cement dilutions and turbidimeter readings. Ten water-cement ratios were chosen ranging from 0.36-0.54 at increments of 0.02. The pastes were first diluted to 1:100, mixed and turbidimeter readings were taken as set forth above. The turbidimeter readings from these ten samples showed a consistent trend. Table 11 sets forth the turbidimeter readings as well as a summary of the relevant statistics for the readings. Average turbidimeter readings varied from 5.5 for a water-cement ratio of 0.36 to 17.4 for a water-cement of 0.54. Low values of coefficient of variation for each measurement indicate the consistency of the test procedure.

TABLE 11

Turbidimeter Readings of Water-Cement Paste with 1:100 Dilution

| Sample No. | w/c ratio | Turbidimeter Reading (range 100) | | | Summary Statistics | | |
|---|---|---|---|---|---|---|---|
| | | Reading 1 | Reading 2 | Reading 3 | Mean | Std. Dev. | Coeff. of Var. |
| 1 | 0.36 | 5.4 | 5.5 | 5.7 | 5.5 | 0.15 | 2.76 |
| 2 | 0.38 | 6.4 | 6.2 | 6.6 | 6.4 | 0.20 | 3.12 |
| 3 | 0.40 | 7.9 | 7.8 | 8.2 | 8.0 | 0.21 | 2.61 |
| 4 | 0.42 | 8.3 | 8.3 | 8.1 | 8.2 | 0.12 | 1.40 |
| 5 | 0.44 | 9.8 | 9.6 | 9.9 | 9.8 | 0.15 | 1.56 |
| 6 | 0.46 | 11.0 | 10.6 | 11.2 | 10.9 | 0.31 | 2.79 |
| 7 | 0.48 | 11.3 | 10.8 | 10.5 | 10.9 | 0.40 | 3.72 |
| 8 | 0.50 | 12.6 | 12.8 | 13.0 | 12.8 | 0.20 | 1.56 |
| 9 | 0.52 | 15.8 | 15.6 | 15.3 | 15.6 | 0.25 | 1.62 |
| 10 | 0.54 | 17.2 | 17.3 | 17.6 | 17.4 | 0.21 | 1.20 |

A linear regression analysis was performed between the water-cement ratios (dependent variable) and corresponding turbidimeter readings (independent variable). The results yielded the following relationship between these variables:

Water-cement Ratio = (1)

$0.29 + 1.54 \times 10^{-2} *$ Turbidimeter Reading
($R^2 = 0.95$, $n = 10$)
Standard error of estimate (SEE) = $1.37 \times 10^{-2}$
Standard error of coefficient = $1.19 \times 10^{-3}$ The high value of coefficient of determination, $R^2$, indicates that there is a significant correlation between the water-cement ratio (with 1:100 dilution) and turbidimeter reading. This experiment was repeated to find whether the relationship described by the above equation was valid. Table 12 shows the results of the replicate experiment. The replicate equation is as below:

$$\text{Water-cement Ratio} = 0.27 + 1.75 \times 10^{-2} * \text{Turbidimeter Reading } (R^2 = 0.95, n=10) \quad (2)$$

TABLE 12

Turbidimeter Readings of Water-Cement Paste with 1:100 Dilution

| Sample No. | w/c ratio | Turbidimeter Reading (range 100) | | | Summary Statistics | | |
|---|---|---|---|---|---|---|---|
| | | Reading 1 | Reading 2 | Reading 3 | Mean | Std. Dev. | Coeff. of Var. |
| 1 | 0.36 | 5.5 | 5.7 | 5.7 | 5.4 | 0.15 | 2.76 |
| 2 | 0.38 | 7.1 | 6.9 | 6.8 | 6.9 | 0.15 | 2.20 |
| 3 | 0.40 | 7.8 | 7.9 | 7.8 | 7.8 | 0.06 | 0.74 |
| 4 | 0.42 | 7.6 | 7.8 | 8.0 | 7.8 | 0.20 | 2.56 |
| 5 | 0.44 | 9.7 | 9.3 | 9.6 | 9.5 | 0.21 | 21.8 |
| 6 | 0.46 | 10.9 | 10.6 | 10.5 | 10.7 | 0.21 | 1.95 |
| 7 | 0.48 | 11.1 | 11.1 | 11.4 | 11.2 | 0.17 | 1.55 |
| 8 | 0.50 | 13.2 | 12.9 | 13.1 | 13.1 | 0.15 | 1.17 |
| 9 | 0.52 | 14.8 | 14.6 | 14.4 | 14.6 | 0.20 | 1.37 |
| 10 | 0.54 | 16.4 | 15.9 | 15.4 | 15.9 | 0.50 | 3.14 |

Figure 6:
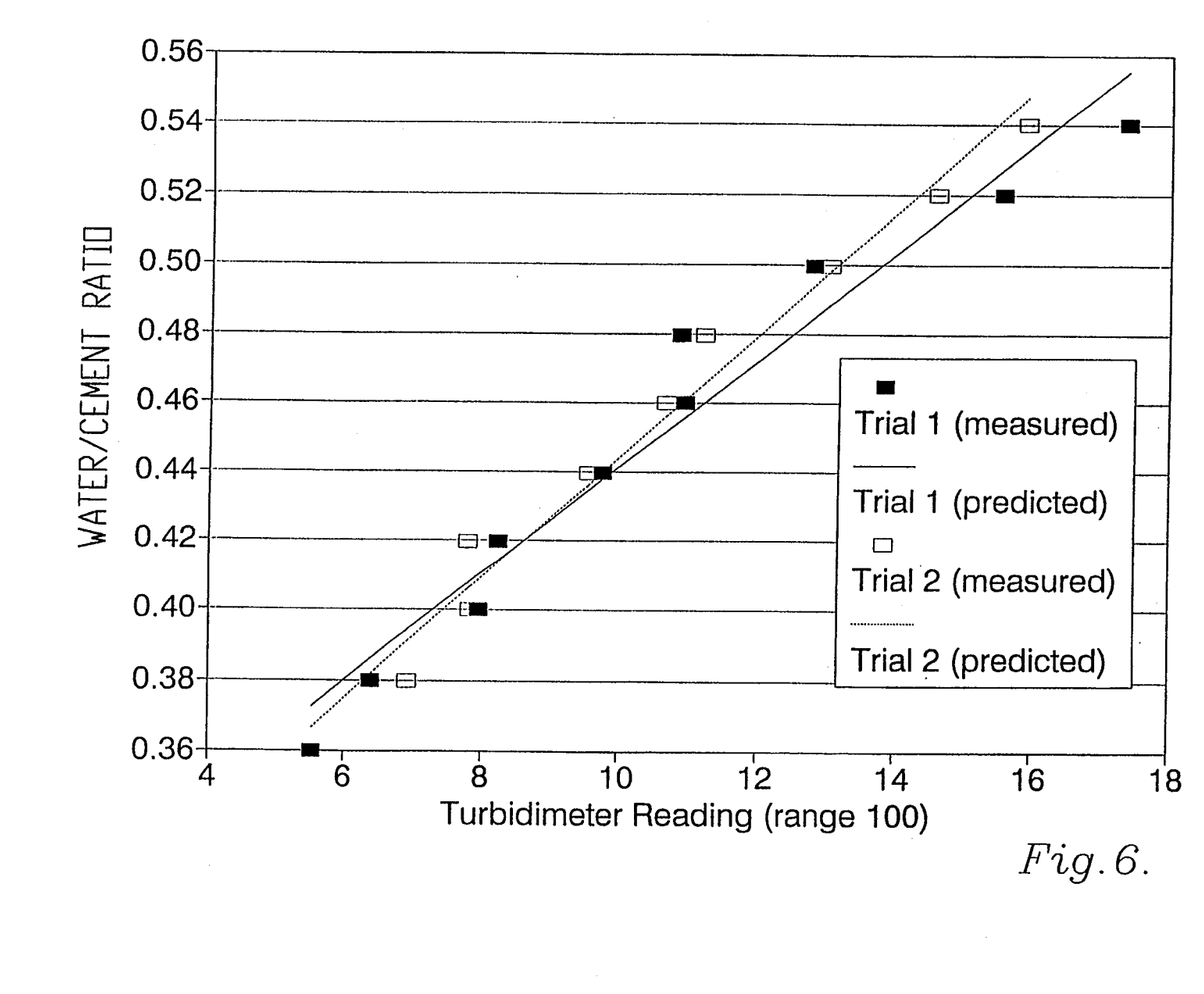
FIG. 6 is a graph of water-cement ratios versus actual and predicted turbidimeter readings employing the regression analysis results described in Example 4.

Standard error of estimate (SEE) = $9.51 \times 10^{-3}$
Standard error of coefficient = $9.26 \times 10^{-4}$ The new equation appeared to describe a better correlated relationship between turbidimeter reading and water-cement ratio. FIG. 6 shows the two equations graphically. The discrepancy in readings for the two trials increases for water-cement ratio higher than 0.42.

EXAMPLE 5

A turbidimeter test was performed on a concrete mix having a mix proportion 1:2:3 by weight (cement:fine aggregate:coarse aggregate) and a density of 639 lb/cu.yd., with water-cement ratios of 0.49 and 0.45. The cement, water, sand and coarse aggregate were first mixed and one pound of the mix was washed successively through #4, #10 and #100 sieves using 5 lb. of water. This was repeated ten times using the same water to create water-cement dilutions. These dilutions were mixed with an automatic mixer for 30 seconds and three turbidimeter readings were taken with each dilution.

Table 13 sets forth the turbidimeter readings for this experiment. The readings are consistently lower than those of Example 4, which is to be expected since the dilution is different, approximately 1:60. Any fine particles attached to the aggregates and the remaining cement particles not completely washed out may also have contributed to the differences in turbidity values.

TABLE 13

| Sample No. | w/c ratio | Turbidimeter Reading (range 100) | | | Statistical Data | | |
|---|---|---|---|---|---|---|---|
| | | Reading 1 | Reading 2 | Reading 3 | Mean | Std. Dev. | Coeff. of Var. |
| 1 | 0.45 | 6.4 | 6.5 | 6.4 | 6.4 | 0.06 | 0.90 |
| 2 | 0.49 | 7.2 | 6.9 | 6.8 | 7.0 | 0.21 | 2.99 |

We claim:

1. Apparatus for determining the water-cement ratio of uncured concrete containing water, cement and aggregate, said apparatus comprising:
means for separating said aggregate from said cement and water, and for creating a dilute dispersion of the cement in added water; and
a turbidimeter operatively coupled with said separating and diluting means for determining the turbidity of said dilute dispersion as a measure of said water-cement ratio.

2. The apparatus of claim 1, said separating and diluting means comprising an upright chamber having sieve means therein for receiving a quantity of said uncured concrete, and means for directing dilution water over said uncured concrete for effecting said separation of aggregate from said cement and water, and for creating said dilute dispersion.

3. The apparatus of claim 2, including conduit means operably coupled between the bottom and top of said chamber for recirculation of said dilution water, there being pump means interposed in said conduit means.

4. The apparatus of claim 3, said turbidimeter being operatively coupled with said conduit means for selective delivery of said dilute dispersion to the turbidimeter for said turbidity determination.

5. The apparatus of claim 2, said sieve means including a plurality of vertically spaced sieve members.

6. The apparatus of claim 5, said sieve members being No. 4, No. 10, No. 50 and No. 100 sieves arranged in vertically descending order.

7. The apparatus of claim 1, including structure for determining the turbidity of said dispersion a plurality of times over a selected time period.

8. The apparatus of claim 7, said time period being up to about 300 seconds.

9. A method for determining the water-cement ratio of uncured concrete containing water, cement and aggregate, said method comprising the steps of:
separating said aggregate from said cement and water, and creating a dilute dispersion of said cement in added water; and
passing said dilute dispersion through a turbidimeter to obtain a turbidimeter value of said dilute dispersion, and generating a value corresponding to said water-cement ratio using said turbidimeter value.

10. The method of claim 9, including the step of placing a quantity of said uncured concrete within an upright chamber including sieve means, and directing said dilution water over said concrete to effect said separation and formation of said dilute dispersion.

11. The method of claim 10, including the step of circulating said dilution water from the bottom to the top of said chamber.

12. The method of claim 9, wherein said dilute dispersion has a water-cement ratio of from about 10-1000.

13. The method of claim 12, said ratio being from about 50-250.

14. The method of claim 10, including the step of passing said uncured concrete through a succession of spaced sieve members for effecting said separation and creation of said dilute dispersion.

15. The method of claim 9, including the step of making successive determinations of the turbidity of said dilute dispersions over a selected time period.

16. The apparatus of claim 15, said time period being up to about 300 seconds.

17. The method of claim 9, including the step of comparing said turbidimeter value to a known turbidimeter value for a standard cement mixture to determine said water-cement ratio.

18. The method of claim 9, including the step of substituting said turbidimeter value into a known equation to generate a value corresponding to said water-cement ratio using said turbidimeter value.

* * * * *